United States Patent [19]

Shepherd

[11] Patent Number: 5,629,432
[45] Date of Patent: May 13, 1997

[54] PREPARATION OF α-ARYL γ-BUTYROLACTONES

[75] Inventor: Robin G. Shepherd, Windsor, England

[73] Assignee: John Wyeth & Brother, Ltd., Maidenhead, England

[21] Appl. No.: 436,186

[22] PCT Filed: Nov. 25, 1993

[86] PCT No.: PCT/GB93/02427

§ 371 Date: May 16, 1995

§ 102(e) Date: May 16, 1995

[87] PCT Pub. No.: WO94/12487

PCT Pub. Date: Jun. 9, 1994

[30] Foreign Application Priority Data

Dec. 3, 1992 [GB] United Kingdom ............... 9225257

[51] Int. Cl.[6] .................................................. C07D 307/26
[52] U.S. Cl. .................. 549/326; 544/335; 544/374; 544/336; 546/139; 546/174; 546/284.7; 540/598; 548/253; 548/255; 548/268.6; 548/315.4; 548/365.7; 549/60
[58] Field of Search .............. 549/326, 60; 546/284.7, 546/174; 544/335, 336, 374; 548/315.4, 268.6, 255, 253, 365.7; 540/139, 598

[56] References Cited

PUBLICATIONS

Cave et al, European Journal of Medicinal Chemistry, Clinica Therapeutica, vol. 21, No. 6, 1986, pp. 487–492.
March, Advanced Organic Chemistry, Third Ed., Mar. 1985, John Wiley & Sons, NY pp. 210–316 (1985).

Nilsson et al., J. Med. Chem., vol. 35, No. 2, 1992, pp. 285–294.

Primary Examiner—Joseph McKane
Assistant Examiner—Richard S. Myers, Jr.
Attorney, Agent, or Firm—Arthur G. Seifert

[57] ABSTRACT

This appliciation discloses a process for preparing a lactone of general formula (I), where R is an optionally substituted phenyl group or an optionally substituted mono- or bicyclic heteroaryl radical which process comprises reacting an anion of a malonate of formula (II) with an ethylene compound of formula (III) Y—CH$_2$—CH$_2$OZ, to give a compound of formula (IV) and hydrolysing the compound of formula (IV) to give a lactone of formula (I). The lactones are of use as intermediates for preparing 5-HT$_{1A}$ binding agents.

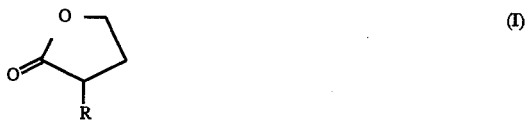

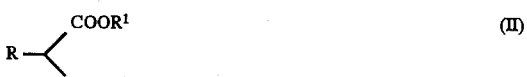

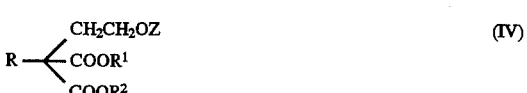

5 Claims, No Drawings

PREPARATION OF α-ARYL γ-BUTYROLACTONES

This is a National Stage filing under 35 U.S.C. 371 of PCT/GB/93/02427, filed Nov. 25, 1993.

This invention relates to lactones, their use and a process for their preparation.

The invention is particularly concerned with the preparation of lactones of the general formula

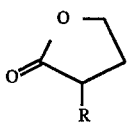
(I)

where R is an optionally substituted phenyl group or an optionally substituted mono- or bicyclic heteroaryl radical containing as the hetero atom or atoms one or more sulphur oxygen or nitrogen atoms, the substituents in the phenyl group or the heteroaryl radical being selected from the group consisting of lower alkyl, lower alkoxy, halogen, halogen halo (lower)alkyl, amino, (lower)alkylamino and di(lower) alkylamino.

The term "lower" as used herein means that the radical referred to contains 1 to 6 carbon atoms. Preferably such radicals contain 1 to 4 carbon atoms. Examples of "lower alkyl" are methyl, ethyl, propyl, isopropyl, butyl, isobutyl and tert.-butyl. Examples of lower alkoxy are methoxy, ethoxy, propoxy and butoxy. An example of halo(lower) alkyl is trifluoromethyl.

Preferably the heteroaryl radical contains 5 to 11 ring atoms. A monocyclic radical may, for example, contain 5 to 7 ring atoms and a bicyclic radical may contain 9 to 11 ring atoms. Preferably the hetero ring contains at least one nitrogen atom as the hetero atom.

Examples of heteroaryl are optionally substituted pyridyl, pyrimidinyl, pyrazinyl, imidazolyl, pyrazolyl, quinolinyl, isoquinolinyl, triazolyl, tetrazolyl, thienyl and furyl.

The lactones of general formula (I) are useful as intermediates for preparing pharmacologically active compounds, for example the 5-HT$_{1A}$ binding agents disclosed in EP-A-0395312, EP-A-0481742 and EP-A-0481744. A particularly preferred lactone of formula I is one in which R is phenyl. This is α-phenyl-γ-butyrolactone, which has the formula

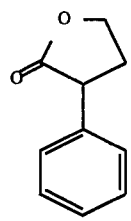
(A)

This may be used as an intermediate in preparing the compounds described and claimed in EP-A-0481744. The compounds of EP-A-0481744 are the racemic and enantiomeric forms of 2,3,4,5,6,7-hexahydro-1-[4-[1-[4-(2-methoxyphenyl)-piperazinyl]]-2-phenylbutyryl]-1H-azepine. The compounds are 5-HT$_{1A}$ binding agents. They may be used, for example, as anxiolytics. The preparation of the compounds from α-phenyl-γ-butyrolactone is illustrated in the reaction scheme below. The reagents and solvents for the individual steps are given for illustrative purposes only and may be replaced by other reagents and solvents known to the man skilled in the art.

REACTION SCHEME

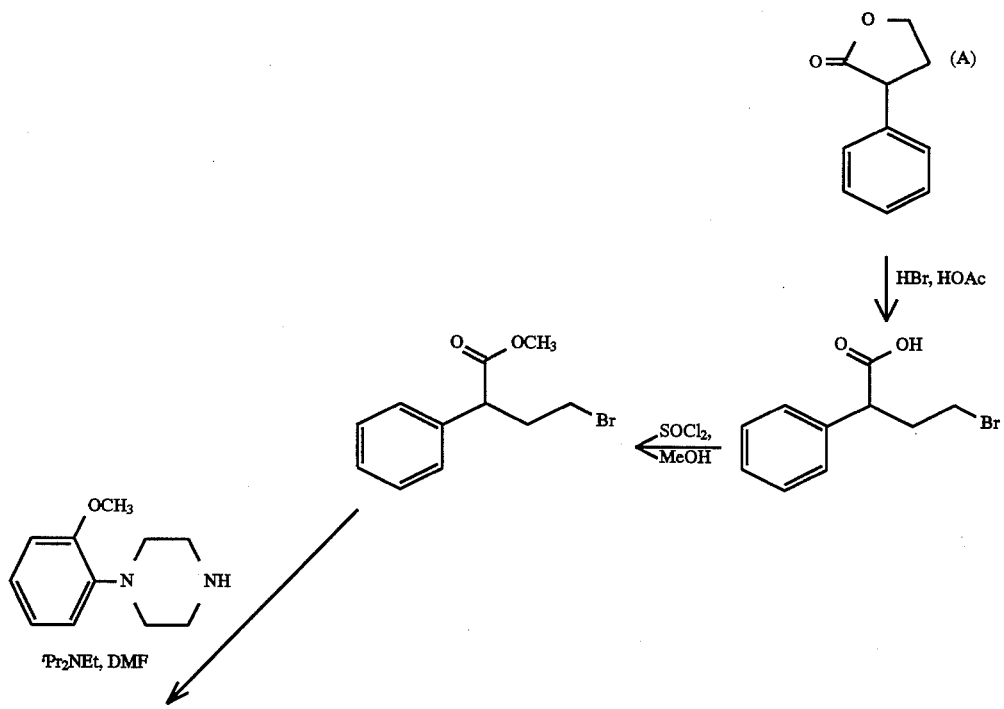

-continued
REACTION SCHEME

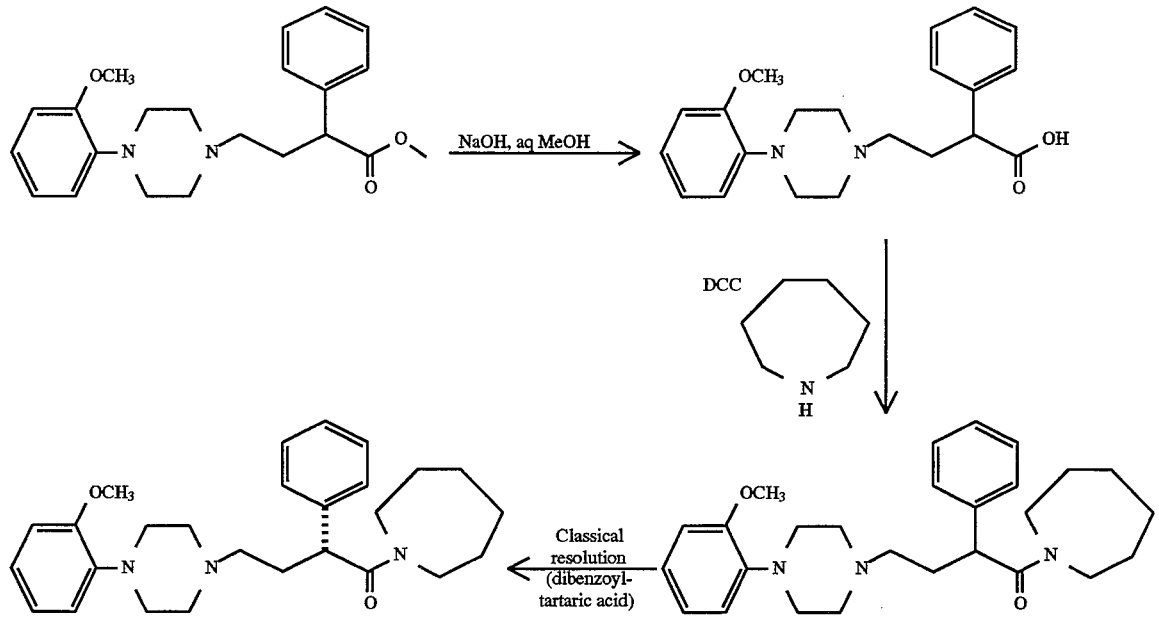

Other compounds of formula (I) may be used in an analogous manner to prepare the compounds of EP-A-0395312 and EP-A-0481742.

Literature references (e.g. Aboul-Enein et al, Indian J. Chem., 1980, 19B, 1083 and Nilsson et al, J. Med. Chem., 1992, 35, 288) disclose the preparation of α-phenyl-γ-butyrolactone by reaction of an ethylene dihalide with diethyl phenylmalonate under basic conditions followed by hydrolysis of the intermediate halo compound of formula

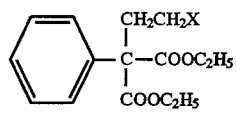

where X is halo.

The process described in the literature gives poor yields of the lactone (due possibly to β-elimination reactions and/or formation of dimers) and/or are unsuitable for preparation of the lactone on a large scale due to the large excess of ethylene dihalide required and/or the necessity of sequential additions of halide/NaH. These disadvantages are overcome (or substantially reduced) by the process of the present invention.

The process described by Cave et al in Eur. J. Med. Chem., 1986, 21, 487–492 for preparing the lactone is similar to the above mentioned literature references except that the intermediate 2-carbethoxy-2-phenyl-γ-butyrolactone is isolated.

According to the present invention lactones of general formula II are prepared by a process which comprises reacting an anion of a malonate of formula (II)

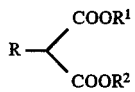

(II)

(where R is as defined above and $R^1$ and $R^2$ are each lower alkyl) with an ethylene compound of formula (III)

$$Y—CH_2CH_2—OZ \qquad (III)$$

(where Y is a leaving group such as halogen, p-toluenesulphonyloxy, methanesulphonyloxy) and Z is a protecting group that is removable under aqueous acidic or basic conditions but is stable in the presence of the malonate anion) to give a compound of formula (IV)

(IV)

(where R, $R^1$, $R^2$ and Z are as defined above) and hydrolysing the compound of formula (IV) to give a lactone of formula (I).

Preferably $R^1$ and $R^2$ are both ethyl.

The anion of the malonate of formula (II) may be prepared by reacting the malonate with a strong base eg alkali metal alkoxide or metal hydride. Preferably the strong base is potassium t-butoxide.

In the ethylene compound of formula III, Y is preferably halo, particularly chloro or bromo. When Y is chloro the reaction can be carried out in presence of a catalytic amount (eg 0.1 eq) of sodium iodide. Examples of the protecting group Z are tetrahydropyran-2-yl, benzoyl and lower alkanoyl. By "lower alkanoyl" is meant an alkanoyl group containing 2 to 6 carbon atoms, preferably 2 to 4 carbon atoms. A preferred lower alkanoyl group is acetyl.

The reaction of the malonate anion and the ethylene compound III may be carried out in an inert solvent such as DMSO, sulpholane, THF or preferably DMF.

The compound of formula IV may be hydrolysed under acidic or basic conditions. Where Z is tetrahydropyran-2-yl the hydrolysis is preferably carried out under basic conditions (e.g. with potassium hydroxide, preferably in the presence of an alcohol eg MeOH) to give an intermediate protected diacid which can then be hydrolysed by acid to the lactone. When Z is lower alkanoyl the hydrolysis is preferably carried out under acidic conditions, e.g. with hydrochloric acid.

The following examples illustrate the invention.

EXAMPLE 1

Diethyl α-phenyl-α-(2-tetrahydropyranyloxyethyl) malonate

Potassium t.butoxide (112 g, 1M) in DMF (800 ml) was treated with diethyl phenylmalonate (236 g, 1M) in DMF (200 ml) then with 1-bromo-2-tetrahydropyranyloxy-ethane (209 g, 1M) in DMF (200 ml). The reaction was heated to 70° C. After 5 hours the reaction was cooled to room temperature, quenched on to water (2.5 l) and 2N HCl (500 ml), and extracted with IPE (1 l, then 500 ml). The organic extracts were washed with water, dried and evaporated to give the title compound (351 g, 96%). Glc 93%+7% unchanged diethylphenylmalonate.

EXAMPLE 2

Diethyl α-phenyl-α-(2-acetoxyethyl)malonate (a) A solution of potassium tert.butoxide (448 g, 4M) in DMF (2 l) under nitrogen at room temperature was treated dropwise with diethyl phenylmalonate (945 g, 4M). 1-Acetoxy-2-bromoethane (668 g, 4M) was added. The reaction was allowed to cool to room temperature after 45 mins and was diluted with water (5 l) then extracted with IPE (2 l, 500 ml). The extracts were washed, dried and evaporated to give the title compound (1300 g). Bp 130°/0.05 mm.

(b) A similar procedure was followed replacing the 1-acetoxy-2-bromoethane with 1-acetoxy-2-chloroethane.

EXAMPLE 3

α-Phenyl-γ-butyrolactone (a) The product of Example 1 (350 g, 0.96M), methanol (500 ml), 25% KOH (600 ml) was heated to reflux for 1 hour. It was then cooled to room temperature and conc. HCl (250 ml, ca 3M) was added dropwise. The reaction was stirred overnight, the methanol removed under vacuum and then extracted with methyl tert. butyl ether (1 l, 200 ml). The organic phase was washed with aqueous NaOH and brine, dried and evaporated to give the title compound (146 g). Distillation gave the product (135 g), b.p 110°–2°/0.2 mm.

(b) The product of Example 2 (837 g, 2.6M) methanol (1.5 l) and 40% aq. NaOH (1 l, 10M) were heated to reflux for 2 hours. The reaction was then cooled to room temperature and acidified with conc. HCl (1 l). The reaction was left as room temperature overnight and then extracted with methyl tert.butyl ether (1 l,500 ml). The extracts were washed with aq. $Na_2CO_3$, dried and evaporated to give the title compound (376 g, 89%).

(c) The product of example 2(a) (1.3 kg), conc.HCl (1 l) and water (1 l) was heated at reflux for 5 h, cooled to room temperature and extracted with methyl t-butyl ether (2 l, 1 l). The organic extracts were washed with aqueous sodium hydroxide solution, dried and evaporated to give the title compound (560 g). Bp 105°/0.05 mm.

EXAMPLE 4

4-bromo-2-phenylbutyric acid

The product of Example 3 (14.5 g, 90 mM) in 48% of HBr/acetic acid (100 ml) was left at room temperature overnight. The reaction was poured onto water (500 ml) and extracted with IPE 2x). The organic phase was washed with water, dried and evaporated to give the crystalline product (22 g) m.p. (cyclohexane).

EXAMPLE 5

Methyl 4-bromo-2-phenylbutyrate

The product of Example 4 (22 g) in methanol (100 ml) was treated dropwise with $SOCl_2$ (7.3 ml, 0.1M) at about 5° C. The reaction mixture was allowed to warm to room temperature. The solvent was evaporated off and the residue partitioned between water and IPE. The organic phase was dried and evaporated to give the title compound as an oil (23 g). Bp. 85°/0.1 mm.

EXAMPLE 6

Methyl 4-[1-[4-(2-methoxyphenyl)piperazinyl]]-2-phenylbutanoate

The product of Example 5 (18.0 g, 70 mM) in DMF (30 ml) was added to 1-(2-methoxyphenyl)-piperazine (13.5 g, 70 mM) and $iPr_2NEt$ (12.3 g, 70 nM) in DMF (150 ml) at room temperature. The reaction mixture was left overnight, diluted with water and extracted twice with IPE. The organic phase was extracted twice with aqueous HCl and the aqueous acid phase basified and extracted with IPE. The organic phase was extracted dried and evaporated to give the title compound (22 g).

EXAMPLE 7

Methyl 4-[1-(4-(2-methoxyphenyl)piperazinyl)]-2-phenylbutanoate

A mixture of the ester from Example 6 (74 g, 0.2M), KOH (16.8 g) and methanol (400 ml) was refluxed 5 h, cooled to room temperature, diluted with water (400 ml) then treated with acetic acid (18 ml). The resulting crystalline product was removed by filtration washed with water and recrystallised from methanol to give the title compound (64 g).

EXAMPLE 8

2,3,4,5,6,7-Hexahydro-1-[4-[1-[4-(2-methoxy) phenyl]piperazinyl-2-phenyl]butyryl-1H-azepine A mixture of the acid from Example 7 (35.5 g, 0.1M), hexamethyleneimine (9.92 g, 0.1M), DCC (20.6 g, 0.1M) and dichloromethane was stirred overnight. The mixture was filtered and the filtrate evaporated to give a crystalline solid which was recrystallised from cyclohexane to give the title compound (40 g).

The product of Example 8 was resolved as described in GB 2248836 to give (−)-2,3,4,5,6,7-hexahydro-1-[4-[1-[(2-methoxy)phenyl]piperazinyl-2-phenyl]butyryl-1H-azepine hydrochloride, m.p. 181°–184° C. $[\alpha]_{26}^{D} = -36°$ (1% in MeOH).

I claim:

1. A process for preparing a lactone of the general formula

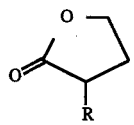

(I)

where R is an optionally substituted phenyl group or an optionally substituted mono- or bicyclic heteroaryl radical containing as the hereto atom or atoms one or more sulphur oxygen or nitrogen atoms, the substituents in the phenyl group or the heteroaryl radical being selected from the group consisting of $C_{1-6}$ alkyl, $C_{1-6}$ alkoxy, halogen, halogen halo($C_{1-6}$)alkyl, amino, ($C_{1-6}$)alkylamino and di($C_{1-6}$ alkyl) amino which process comprises reacting an anion of a malonate of formula (II)

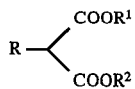
(II)

(where R is as defined above and $R^1$ and $R^2$ are each $C_{1-6}$ alkyl) with an ethylene compound of formula (III)

$Y-CH_2CH_2-OZ$ (III)

(where Y is a leaving group and Z is a protecting group that is removable under aqueous acidic or basic conditions but is stable in the presence of the malonate anion) to give a compound of formula (IV)

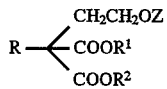
(IV)

(where R, $R^1$, $R^2$ and Z are as defined above) and hydrolysing the compound of formula (IV) to give a lactone of formula (I).

2. A process as claimed in claim 1 wherein R is phenyl.

3. A process as claimed in claim 1 wherein R is a heteroaryl radical selected from optionally substituted pyridyl, pyrimidinyl, pyrazinyl, imidazolyl, pyrazolyl, quinolinyl, isoquinolinyl, triazolyl, tetrazolyl, thienyl and furyl.

4. A process as claimed in claim 1 in which Y is halogen, p-toluenesulphonyloxy or methanesulphonyloxy.

5. A process as claimed in claim 1 in which Z is tetrahydropyran-2-yl, benzoyl or $C_{2-6}$ alkanoyl.

* * * * *